United States Patent [19]

Dolby et al.

[11] Patent Number: 5,675,019

[45] Date of Patent: Oct. 7, 1997

[54] PROCESS FOR MAKING PILOLOCTAM AND DERIVATIVES THEREOF

[75] Inventors: Lloyd J. Dolby; Nestor A. Fedoruk; Shervin Esfandiari, all of Eugene, Oreg.; Michael E. Garst, Newport Beach, Calif.

[73] Assignee: Allergan, Waco, Tex.

[21] Appl. No.: 685,897

[22] Filed: Jul. 18, 1996

[51] Int. Cl.$^6$ .................................................. C07D 207/267
[52] U.S. Cl. ............................................................ 548/551
[58] Field of Search ............................................. 548/551

[56] References Cited

U.S. PATENT DOCUMENTS

| | | | |
|---|---|---|---|
| 3,470,197 | 9/1969 | VanDyke, Jr. | 260/309 |
| 5,055,467 | 10/1991 | Albaugh | 514/235.8 |
| 5,198,545 | 3/1993 | Albaugh | 544/133 |
| 5,264,449 | 11/1993 | Albaugh | 514/397 |
| 5,453,434 | 9/1995 | Albaugh et al. | 514/397 |

OTHER PUBLICATIONS

DeGraw, J.I., "Prostaglandins, An Improved Synthesis of Pilocarpine," Tetrahedron., vol. 28, 1972, pp. 967–972.
Koda et al, "Synthesis of Analogs related to Pilocarpine", Journal of Pharmaceutical Sciences, Dec. 1973, vol. 62, No. 12, pp. 2021–2023.
Sauerberg et al, "Cyclic Carbamate Analogues of Pilocarpine", J. Med. Chem. 1989, 32, pp. 1322–1326.
Kondo et al, "Synthesis of y–Lactones By The Condensation of 2–Alkene–1, 4–Diols With Orthocarboxylic Esters", Chemistry Letters, pp. 741–742, 1974.
Noordam et al, "Stereoselective synthesis (+)–pilocarpine, an imidazole alkaloid used in ophthalmology", Recl. Trav. Chim. Pays–Bas 98, pp. 425–470.
Dey, A.N., "The Jaborandi Alkaloids. Part I. The Synthesis of Homo–and isoHomo–pilopic Acids and of r–Pilocarpidine and r–isoPilocarpidine by New Methods and the Resolution of r–Pilocarpine, S. Chem. Soc.", (1937), pp. 1057–1065.
Birch et al, "Reduction by Metal–Ammonia Solutions and Related Reagents", Advanced Organic Chemistry, No. 8, pp. 1–65 (1972).
Benkeser et al, "Reduction of Organic Compounds by Lithium in Low Molecular Weight Amines. VII. The Preparation of Dihydroaromatics. A Comparison of the Lithium–Amine and Birch Reduction Systems", Journal of Organic Chemistry, 28, pp. 1094–1096, 1972.
Kaiser, E.M., "A Comparison of Methods Using Lithium/Amine and Birch Reduction Systems", Synthesis, 1972, pp. 391–415.

*Primary Examiner*—Mukund J. Shah
*Assistant Examiner*—Bruck Kifle
*Attorney, Agent, or Firm*—James Mark Hoch; Robert J. Baran; Martin A. Voet

[57] ABSTRACT

A process of preparing lactam derivatives of pilocarpine is disclosed. The process involves condensation of a dihydroxybutene and alkyl orthoester to form a lactone intermediate which is oxidized to trans-pilopic acid. This lactone ring is reacted with a benzylamine and the benzyl group removed with a novel dissolving metal reduction mixture to yield the key intermediate IV

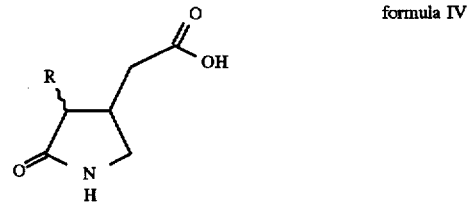

formula IV which can be elaborated to pilolactam through a known sequence of steps.

19 Claims, No Drawings

PROCESS FOR MAKING PILOLOCTAM AND DERIVATIVES THEREOF

CROSS REFERENCE TO RELATED APPLICATIONS

Commonly assigned U.S. patent application Ser. No. 08/685,902, entitled "Improved Lithium and Amine Dissolving Metal Reduction" which has been filed on the same day as the present application in the names of Lloyd J. Dolby, Nestor A. Fedoruk, Shervin Esfandiari, Natalie C. Chamberlain and Michael E. Garst is directed to the process of using a combination of lower alkylamine and ethylene diamine with lithium to effect reductions of organic compounds. The contents of this copending application are incorporated herein by reference in their entirety.

BACKGROUND OF THE INVENTION

1. Field of the Invention

The present invention relates to new processes for making 1-methyl-1H-imidazol-5-yl-methyl-2-pyrrolidinones which have valuable pharmacological properties, especially in the area of ophthalmology.

2. Description of the Related Art (+)-Pilocarpine is an alkaloid which derives its basic properties from the imidazole ring in its structure. It has received a certain amount of attention from the viewpoint of synthesis because it has pharmacological significance. (+)-Pilocarpine has found use in ophthalmology as an antiglaucoma agent and miotic and is generally classified as a cholinergic or parasympathomimetic with muscarinic receptor stimulating properties. It is obtained by the extraction of jaborandi leaves, mainly Pilocarpus microphyllus Stapf., which is indigenous to South America. The cost of pilocarpine from chemical supply companies is quite high, which reflects the cost of extracting and purifying a natural product from plant material.

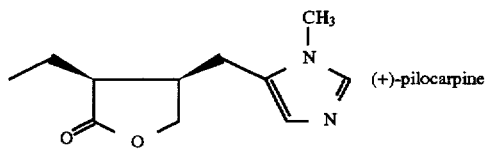

(+)-pilocarpine

Older syntheses of pilocarpine have been laborious undertakings with concomitant low yields. Some more recent syntheses which employ (L)-histidine as a starting material have given yields of (+)-pilocarpine at about 25%. [Noordam, Maat and Beyerman, *Recl. Tray. Chim. Pays-Bas*, 98 (7–8), 425–470 (1979)]. Other syntheses are known, one of the more classical synthetic approaches proceeds through the intermediate, homopilopic acid and was utilized for making $^{14}$C labeled pilocarpine by DeGraw, Engstrom and Willis, *J. Pharm. Sci.*, 64 (10), 1700–1 (1975), [see also DeGraw, J. I., *Tetrahedron*, 28, 967–972 (1972)]. Resolution of stereoisomers of pilocarpine is known, see, for example, A. N. Dey, *J. Chem. Soc.*, p. 1057, (1937)

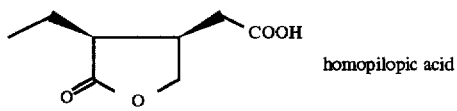

homopilopic acid

Several commonly assigned patents and pending applications in the name of Albaugh concern the making and use of lactam derivatives of pilocarpine. They are made by reacting pilocarpine with an amine to effect a ring opening and replacement of the lactone oxygen with a nitrogen atom. These derivatives have structures as represented in FIG. 1.

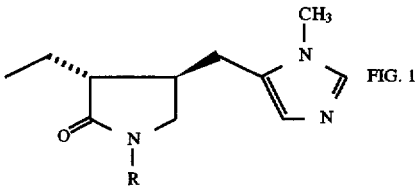

FIG. 1

U.S. Pat. No. 5,055,467, entitled "Pharmaceutical Epinephrine-Pilocarpine Compounds", which issued on Oct. 8, 1991, in the name of Pamela Albaugh, and U.S. Pat. No. 5,198,545, entitled "Novel Pharmaceutical Epinephrine-Philocarpine Derivatives", which issued on Mar. 30, 1993, in the name of Pamela Albaugh, concern the making and use of pilocarpine lactams covalently linked with epinephrine or its derivatives. The linkage is made at the lactam ring nitrogen through an acyl group and the hydroxyl group of epinephrine, which is represented by "R" in FIG. 1. The entire contents of these two patents are incorporated herein by reference.

U.S. Pat. No. 5,264,449, entitled "N-Substituted Derivatives of 3R, 4R-Ethyl-[(1-Methyl-1H-Imidazole-5-YL)Methyl]-2-Pyrrolidinone", which issued on Nov. 23, 1993, in the name of Pamela Albaugh and pending application Ser. No. 08/126,285, entitled "N-Substituted Derivatives on 3R, 4R-Ethyl-[(1-Methyl-1H-Imidazole-5-YL)Methyl]-2-Pyrrolidinone", which was filed on Sep. 20, 1993, in the name of Pamela Albaugh and U.S. Pat. No. 5,453,434, entitled "N-Substituted Derivatives of 3R, 4R-Ethyl-[(1-Methyl-1H-Imidazol-5-YL)Methyl]-2-Pyrrolidone", which issued on Sep. 26, 1995, in the name of Pamela Albaugh, Gregory White and Michael Garst concern the making and use of other derivatives which function as pro-drugs of FIG. 1 wherein R is a variety of different acyl groups which are hydrolyzed in vivo to give isopilolactam (R=H). The contents of this patent and these applications are incorporated herein by reference in their entireties.

U.S. Pat. No. 3,470,197, to Van Dyke, discloses lactam ring derivatives of pilocarpine and isopilocarpine and a method of making such compounds. The method concerns heating ammonia or a primary amine in a hydroxylic solvent such as ethanol or isopropanol at elevated temperature and pressure. Typically the reactions were performed in an autoclave.

Koda, et al. investigated lactam analogs of pilocarpine as well as analogs wherein the carbonyl group of the lactone ring was reduced to a methylene group. Both of the these types of compounds were reported to have biological effects, however the authors concluded that "pilocarpine analogs in which the lactone ring was modified further substantiated the observation that an intact ring structure (lactone or its equivalent) is necessary for biological activity". [Koda, R. T., Dea, F. J., Fung, K., Elison, C., and Biles, J. A.; *J. Pharm. Sci.* 62(12), pp. 2021–2023 (1973)]

Sauerberg, et al. made cyclic carbamate analogs of pilocarpine starting from ring benzylated histidine. Certain of these compounds displayed the cholinergic muscarinic activity exhibited by pilocarpine and were said to be hydrolytically more stable than pilocarpine and therefore good candidates as drugs for the treatment of glaucoma. [Sauerberg, P., Chen, J., WoldeMussie, E., and Rapoport, H.,

*J. Med. Chem.* 32, pp. 1322–1326 (1989)]. Since the ring carbon at position 3 of the lactone ring was replaced with a nitrogen this removed the need for control of that stereochemical center in the reaction. The other stereocenter was determined by the configuration of the starting material, L-histidine.

U.S. Pat. No. 5,264,449 (to Albaugh) discloses that isopilolactam (i.e. the trans configuration) is more preferred in topical treatment of glaucoma than pilolactam (the cis configuration). This is advantageous since the trans configuration is favored in the present reaction and since the cis form does isomerize to the trans form by the action of heat or alkaline media (see DeGraw, cited above in *Tetrahedron,* 28, p. 967].

Kondo, et al. [Chemistry Letters pp. 741–2, 1974]disclose a condensation reaction of 1,4-dihydroxybutene and ortho esters to produce vinyl substituted lactones.

In view of the above, it is apparent that an inexpensive and preparatively useful synthesis of pilolactam from readily available starting materials is desirable. Further, the products of such a synthesis would be useful in the pharmaceutical arts, especially in the treatment of glaucoma.

Therefore, it is one objective of this invention to provide a lower cost, synthetically useful process for obtaining isopilolactam and pilolactam from readily available and inexpensive starting materials.

It is a further object of the invention to provide a selective and high-yield method of removing benzylic protecting groups from the lactam intermediate which is formed in the process of this synthesis.

SUMMARY OF THE INVENTION

The present invention covers processes for making isopilolactam and/or pilolactam, which are useful generally as muscarinic agonists and as anti-glaucoma medications in particular. The pilolactams are also useful for making derivatives which have superior topical activity in treating glaucoma in comparison to the unsubstituted compounds themselves. The process by which the pilolactams are made is through the reaction of an alkyl ortho-ester of the formula $R'C(OR_1)_3$ wherein R' is hydrogen or a $C_1$ to $C_6$ alkyl and $R_1$ is methyl or ethyl and trans-1,4-dihydroxy-2-butene to effect a condensation reaction and subsequent Cope rearrangement of the intermediate formed to yield a compound of formula I,

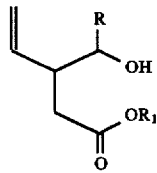

formula I which cyclizes under the reaction conditions to give the key lactone intermediate of formula II in which the ratio of trans isomer to cis isomer formed is around 85/15. Constant removal of by-produced alcohol from the reaction mixture promotes formation of the lactone product.

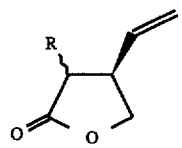

formula II

The lactone intermediate is treated with diborane and then hydrogen peroxide to form the primary alcohol which is further oxidized by chromium trioxide (Jones reagent) to yield homopilopic acid, or an analog, of formula III as a mixture of trans and cis isomers in a ratio of about 85/15.

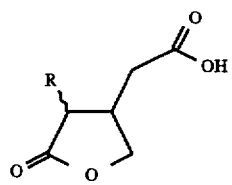

formula III

Formula III, which is also known as trans-homopilopic acid when R=ethyl, is heated with a benzylamine and the resulting N-benzyl-lactam is reduced by treatment with lithium in $R_2$—$NH_2$, wherein $R_2$ is a $C_1$ to $C_6$ alkyl radical, e.g. t-butylamine and ethylenediamine to a secondary lactam of formula IV,

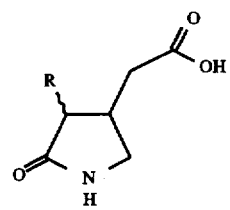

formula IV thereafter the structure of formula IV is subsequently converted to the acyl chloride and made to react with di-t-butylacetamidomalonate, which is subsequently hydrolyzed in acid to form an aminomethyl ketone of formula V.

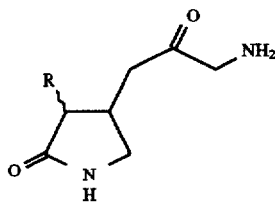

formula V

Treatment of the aminomethyl ketone (V) with methyl isothiocyanate gives a methylthiourea which is cyclized to an imidazolylthiol with acid and subsequently the thiol group removed from the ring by oxidation with hydrogen peroxide, or by stirring in solution with Raney nickel.

The present process for reducing a tertiary lactam uses lithium metal as an electron source, lower alkyl amines as solvent and ethylenediamine (1,2-diaminoethane) as the cosolvent. Lithium is dissolved in the alkyl amine along with at least one equivalent of ethylenediamine per gram-atom of lithium.

Temperatures at which the reaction can be run vary from −20° C. to 65° C. Preferred temperatures for the practice of the present invention are from 0° C. to 55° C., with the most preferred temperature being at or about room (ambient) temperature. The reaction is run at ambient (atmospheric) pressure, and so, in any case, the reaction temperature cannot be above the boiling point of the reaction solution chosen.

Preferred alkyl amines for use in the present invention are n-propylamine, isopropylamine and t-butylamine. Most preferred of these amines for use in the present process is n-propylamine, however, t-butylamine is preferred when there is a need for a non-nucleophilic amine such as in reductions of N-benzyl-amides. The more lipophilic nature of these alkyl amines allows better solvation of the organic substrate.

The order of addition of the reactants to the alkyl amine-ethylenediamine solvent can vary. Lithium can be added first to the mixture, or in portions after addition of the organic substrate. If the reaction is exothermic, solvent can easily be returned to the reaction mixture by equipping the reaction flask with a water-cooled reflux condenser.

Reaction times vary with different conditions and substrates being reduced, but are of sufficient length to allow the starting materials to be reduced to the desired products, but not of such a length of time to allow unwanted double bond isomerizations or side reactions to occur. Monitoring of reaction progress is routinely conducted in the practice of synthetic chemistry and varies with the type of reaction. Examples of methods used in monitoring are thin layer chromatography, proton NMR, fluorescence spectrophotometry and measurement of solution pH. One skilled in the art knows which method to select depending on the starting materials, products and conditions utilized in running the reaction. Generally, after all of the lithium metal has dissolved into the solvent, the reaction is considered to have finished. Time spans of between 5 minutes and 24 hours are typically required.

Once the reaction is complete, the solvent phase is customarily removed under reduced pressure, typically on a rotary evaporator, which allows recovery of the solvents from the reaction mixture. After evaporation, a semisolid or viscous oil remains. This residue is treated with water, which in some reactions can be quite exothermic, to dissolve or dilute the residue. An organic solvent that is immiscible in water yet has the necessary solubilization characteristics to dissolve the product of the reaction is then added to the aqueous mixture. One skilled in the art of synthetic chemistry is knowledgeable in the selection of suitable solvents for the dissolution and extraction of a given compound or class of compounds.

DETAILED DESCRIPTION OF THE INVENTION

Definitions:

As used in the description of this invention the following definitions apply to the terms cis-pilocarpine, trans-pilocarpine, pilolactam and isopilolactam. Cis-pilocarpine is another way of describing (+)-pilocarpine as shown in the labeled structure above. It indicates that both substituents at the two and three positions of the lactone are located on the same side of the plane formed by the lactone ring. Trans-pilolactam indicates that the ethyl substituent at the 2-position of the lactone is shifted to the other side of the plane of the ring from the methylene bearing the methyl-imidazole group at position-3. Another name for trans-pilocarpine is isopilocarpine. In a similar fashion, pilolactam has the same ring substitution pattern as cis-pilocarpine [(+)-pilocarpine], but differs in that a nitrogen atom replaces the oxygen atom in the ring. It is the lactam analog of pilocarpine, hence the name pilolactam. Isopilolactam by analogy to isopilocarpine is the trans-isomer of pilolactam.

In the art, homopilopic acid refers to an intermediate structure represented by formula III wherein R is ethyl and the substituents in the 2 and 3 position of the ring are in the cis orientation. Trans-homopilopic acid is used to designate the trans isomer.

In terms of indicating the position of substituents on the lactone or lactam rings of the present invention, $\alpha$ indicates an isomer wherein the substituent is above the plane defined by the ring and $\beta$ indicates that the substituent is located below that plane.

Preferred compounds produced by the process of the invention for use in ophthalmology are the trans isomers, i.e. trans pilolactam and derivatives and analogs thereof.

The following nonlimiting examples further illustrate the practice of the invention.

EXAMPLES

Example 1 trans-homopilopic acid

A. Compound of formula II (R=ethyl)

A mixture of trans-1,4-dihydroxy-2-butene (8.8 g, 0.1 mol), trimethylorthobutyrate (29.6 g, 0.2 mol) and hydroquinone (1.1 g, 0.01 mol) were heated at 140°–150° C. under continuous removal of methanol for 22 hrs. Distillation gave 7 g of trimethylorthobutyrate boiling at 55°–65° C. (~12 mm Hg) and 12 g (74%) of lactone boiling at 105°–110° C. (~12 mm Hg). A gas chromatograph analysis of the lactone fraction showed it was 86% pure (the largest part of the impurity was trimethylorthobutyrate) and the ratio of trans to cis lactone was 85/15.

B. Hydroboration and oxidation

In a 3-necked flask under $N_2$ was placed 70 mL of 1N solution of diborane in THF and the flask was placed in an ice and salt methanol bath 2-Methyl-2-butene (17 mL, 0.154 mol) was added to 25 mL of tetrahydrofuran (THF) and added dropwise to the diborane solution over a span of 10 minutes. The mixture was then stirred for 1 hr. at 0° C. The reagent mixture was then returned to the ice and salt methanol bath and a solution of the lactone from step A (9.8 g, 0.07 mol) in 25 mL of THF was added all at once. The reaction mixture was permitted to warm to room temperature over a period of 1 hr to complete the hydroboration. The mixture was then cooled to 0° C. and 23 mL of 3N NaOH was added followed by dropwise addition of 23 mL of 30% $H_2O_2$. After stirring for 20 rain at room temperature, the solution was extracted with two 100 mL portions of diethyl ether. The combined ether extracts were evaporated and the residue was acidified and extracted with two 25 mL portions of ether which were concentrated to give~9 g of residue. A peroxide test gave a positive result, so the oil was dissolved in 50 mL of ether and the solution was washed with two 25 mL portions of 5% $NaHSO_3$ solution. The ether was again evaporated and the residue distilled under vacuum at~0.1 mm Hg. The first fraction of 1.1 g which distilled between 55°–90° C. was mostly the starting lactone. A second fraction boiling between 90°–100° C. weighed 1 g and was mostly the desired alcohol and the pot residue which weighed 1 g was pure alcohol.

C. Jones oxidation of the alcohol of part B.

The alcohol (0.48 g, 0.003 mol) was dissolved in 15 mL of acetone and 1 mL of Jones reagent ($H_2CrO_4$) was added. The mixture was stirred at water-bath temperature for 1 hr. and then excess Jones reagent was destroyed by addition of isopropanol. Next, 20 mL of water was added and the solution was extracted with 3 portions (25 mL each) of ether. The combined ether portions were evaporated to give 0.4 g of an oil. This oil was distilled through a molecular still apparatus to give 0.23 g of an oil which solidified. The solid had a m.p. of 43°–53° C. The Jones reagent was prepared by dissolving 13.36 g of $CrO_3$ in 11.5 mL of conc. $H_2SO_4$ and diluting with distilled $H_2O$ to a volume of 50 mL.

Example 2

Isopilocarpine

In the same manner as described by Degraw in *Tetrahedron*, 28, on page 971 the product of Example 1 is converted to the aminomethylhomo pilopylketone and subsequently reacted with methylisothiocyanate, cyclized and desulfurized using Raney nickel, or hydrogen peroxide oxidation.

Example 3 trans-N-benzylpilolactam

Pilocarpine hydrochloride (98 g, 0.40 mol) and 300 g (2.8 mol) of freshly distilled benzylamine was heated under reflux in a nitrogen atmosphere for 40 hr. After 22 hr, the reaction mixture contained about 12% pilocarpine. The cooled reaction mixture was treated with 100 mL of 3N sodium hydroxide and the layers were separated. The aqueous layer was washed with two 100 mL portions of methylene chloride. The combined organic material was washed twice with water and the methylene chloride was evaporated. The benzylamine was distilled from the product at 75° C. (0.15 mm Hg). The gas chromatogram showed 2% pilocarpine, 74% trans-N-benzylpilolactam, and 10% of a material eluting near the major product which may be the cis-isomer of N-benzylpilolactam. The remaining material consisted of a number of minor impurities. The crude material was used directly in the next step.

Example 4 trans-pilolactam

Debenzylation with lithium in n-propylamine. A solution of trans-N-benzyl-lactam (29.7 g, 0.1 mol) in 400 mL of n-propylamine and 40 mL of ethylenediamine in a three-neck flask fitted with a stirrer under nitrogen was cooled to 0° C. in an ice bath. Lithium (7.0 g, 1.0 mol) in small pieces was added quickly to the solution. After 20 min. the internal temperature rose to 20° C. and remained there for 1 hour. When the temperature began to drop, the ice bath was removed. After an additional 4 hr, all of the lithium was gone. The reaction developed a deep maroon color. The volatile amines were evaporated on the rotovap and 300 mL of cold water was cautiously added to the residue. This process was very exothermic. The aqueous solution was extracted three times with 100 mL portions of ether which removed the majority of the impurities and only a trace of the product. Three extractions with 100 mL portions of chloroform afforded 19 g of crude product after evaporation of the solvent. The gas chromatogram showed 93% of the desired isopilolactam.

Example 5 trans-pilolactam

In an analogous fashion to Examples 3, a benzylamine and the product of Example 1 is condensed to form the N-benzylated lactam derivative of trans-pilopic acid. The benzylated lactam is then reduced to the intermediate of formula III by treatment with lithium in an alkylamine and ethylenediamine similarly to the procedure of Example 4.

Example 6

N-benzyl-lactam derivative of Example 1, Part A

Two equivalents of benzylamine are heated with two equivalents of an ortho ester, such as trimethylorthobutyrate to form the amide acetal. The resulting amide acetal is condensed as in Example I, Part A with trans-1,4-dihydroxy-2-butene in the presence of hydroquinone. The mixture is heated and by-product alcohol is removed continuously from the reaction mixture to produce the title compound.

The invention has been described by reference to certain preferred embodiments and to examples; however, it should be understood that it may be embodied in other specific forms or variations thereof without departing from its spirits or essential characteristics. The embodiments described above are therefore considered to be illustrative in all respects and not restrictive, the scope of the invention being indicated by the appended claims rather than by the foregoing disclosure.

We claim:

1. A process of making

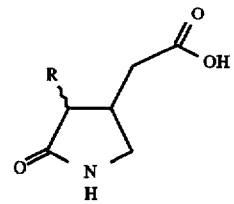

formula IV which is useful in the synthesis of isopilolactam, pilolactam and derivatives thereof, comprising the steps of:

(1) reacting trans-1,4-dihydroxy-2-butene with an ortho ester, $R'C(OR_1)_3$, wherein R' is hydrogen or $C_1$ to $C_6$ alkyl, and $R_1$ is methyl or ethyl, in the presence of hydroquinone to form a compound of formula I

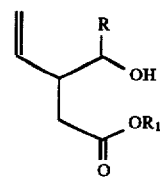

formula I wherein R is hydrogen, methyl or ethyl;

(2) cyclizing, with further heating, to a compound of formula II wherein the wavy line represents either the α or β configuration;

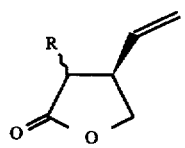

formula II (3) treating the lactone intermediate of formula II in sequence with diborane, hydrogen peroxide and oxidation with chromium trioxide (Jones reagent) to yield trans-pilopic acid or analog of formula III;

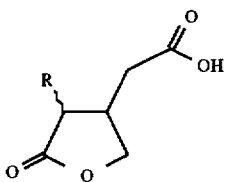

formula III (4) condensing the trans-pilopic acid or analog with a benzylamine by heating; and (5) reducing the resulting N-benzylated lactam to a secondary lactam of formula IV

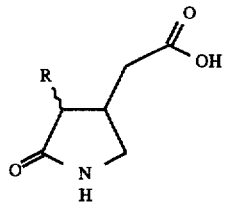

formula IV by treatment with lithium in a mixture of $R_2\text{-}NH_2$, wherein $R_2$ is $C_1$ to $C_6$ alkyl, and ethylenediamine.

2. The process of claim 1 wherein R' is n-propyl.
3. The process of claim 1 wherein R' is ethyl.
4. The process of claim 1 wherein $R_2$ is n-propyl.
5. The process of claim 1 wherein about 1 molar equivalent of ethylenediamine is employed in step (5), i.e. reducing the tertiary lactam.
6. The process of claim 1 wherein about 10 molar equivalents of lithium is employed in step (5), i.e. reducing the tertiary lactam.
7. The process of claim 1 wherein the condensation of trans-1,4-dihydroxy-2-butene with the ortho ester and subsequent cyclization is promoted by continuous removal of by-produced alcohol from the reaction mixture.
8. The process of claim 1 wherein the order of the steps is changed to proceed in the order: (1), (2), (4) and (3).
9. The process of claim 1 wherein the benzylamine is chosen from the group consisting of benzylamine and α-methylbenzylamine.
10. A process of reducing an N-benzyl-lactam to a secondary lactam comprising exposing the N-benzyl-lactam to a solution of lithium in $R_2\text{-}NH_2$ wherein $R_2$ is chosen from the group consisting of ethyl, propyl, and butyl, including all straight and branched chain isomers thereof, and ethylenediamine, for a time sufficient to effect reduction.
11. The process of claim 10 wherein $R_2$ is n-propyl.
12. The process of claim 10 wherein about 1 molar equivalent of ethylenediamine is employed in step (5), i.e. reducing the tertiary lactam.
13. The process of claim 10 wherein about 10 molar equivalents of lithium is employed in step (5), i.e. reducing the tertiary lactam.
14. A process of converting a lactone ring of pilocarpine or a derivative thereof or a pilopic acid or a derivative thereof to a secondary lactam analog comprising condensing the lactone with a benzylamine to form a tertiary lactam and reducing said lactam in a solution of lithium in $R_2\text{-}NH_2$ wherein $R_2$ is chosen from the group consisting of ethyl, propyl, and butyl, including all straight and branched chain isomers thereof, and ethylenediamine, for a time sufficient to effect reduction.
15. The process of claim 14 wherein $R_2$ is n-propyl.
16. The process of claim 14 wherein about 1 molar equivalent of ethylenediamine is employed in reducing the tertiary lactam.
17. The process of claim 14 wherein about 10 molar equivalents of lithium is employed in reducing the tertiary lactam.
18. The process of claim 14 wherein the benzylamine is chosen from the group consisting of benzylamine and α-methylbenzylamine.
19. A process of preparing the lactam of formula VI comprising

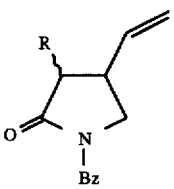

formula VI reacting trans-1,4-dihydroxy-2-butene and

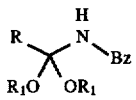

wherein R' is or $C_1$ to $C_3$ alkyl, R is hydrogen, methyl or ethyl and $R_1$ is methyl or ethyl, and Bz is benzyl or α-methylbenzyl, in the presence of hydroquinone to effect condensation, rearrangement and cyclization to the compound of formula VI.

* * * * *

UNITED STATES PATENT AND TRADEMARK OFFICE
CERTIFICATE OF CORRECTION

PATENT NO. : 5,675,019
DATED : October 7, 1997
INVENTOR(S) : Dolby et al

It is certified that error appears in the above-indentified patent and that said Letters Patent is hereby corrected as shown below:

Column 1, line 51; delete "Tray." and insert in place thereof --Trav.--
Column 6, line 43; delete "rain" and insert in place thereof --min--

Signed and Sealed this

Seventeenth Day of February, 1998

Attest:

BRUCE LEHMAN

*Attesting Officer*  *Commissioner of Patents and Trademarks*